(12) United States Patent
Eyal et al.

(10) Patent No.: US 11,324,403 B2
(45) Date of Patent: May 10, 2022

(54) NEWBORN TEMPERATURE AND HEART MONITOR APPARATUS AND METHOD

(71) Applicant: University of South Alabama, Mobile, AL (US)

(72) Inventors: Fabien Gabriel Eyal, Mobile, AL (US); Om Prakash Jha, Mobile, AL (US)

(73) Assignee: University of South Alabama, Mobile, AL (US)

( * ) Notice: Subject to any disclaimer, the term of this patent is extended or adjusted under 35 U.S.C. 154(b) by 0 days.

(21) Appl. No.: 16/382,819

(22) PCT Filed: Oct. 12, 2017

(86) PCT No.: PCT/US2017/056262
§ 371 (c)(1),
(2) Date: Apr. 12, 2019

(87) PCT Pub. No.: WO2018/071621
PCT Pub. Date: Apr. 19, 2018

(65) Prior Publication Data
US 2021/0275029 A1    Sep. 9, 2021

(51) Int. Cl.
*A61B 5/01* (2006.01)
*A61B 5/271* (2021.01)
*A61B 5/318* (2021.01)
*A61B 5/00* (2006.01)

(52) U.S. Cl.
CPC .............. *A61B 5/01* (2013.01); *A61B 5/271* (2021.01); *A61B 5/318* (2021.01); *A61B 5/6805* (2013.01); *A61B 5/6832* (2013.01); *A61B 2503/045* (2013.01)

(58) Field of Classification Search
CPC ......... A61B 5/01; A61B 5/6805; A61B 5/318; A61B 5/271; A61B 5/6832; A61B 5/6804; A61B 2503/045; A61B 2503/04
See application file for complete search history.

(56) References Cited

U.S. PATENT DOCUMENTS

| | | | |
|---|---|---|---|
| 6,927,316 B1 | 8/2005 | Faries, Jr. et al. | |
| 2002/0124295 A1 | 9/2002 | Fenwick et al. | |
| 2008/0114220 A1* | 5/2008 | Banet ................... | A61B 5/6833 600/301 |
| 2010/0076337 A1 | 3/2010 | Medina | |

(Continued)

OTHER PUBLICATIONS

Sampson, M (2016). Understanding the ECG. Part 9: Myocardial ischaemia and infarction (part B). British Journal of Cardiac Nursing. 11 (7), pp. 332-343. https://doi.org/10.12968/bjca.2016.11.7.332 (Year: 2016).*

(Continued)

*Primary Examiner* — Sean P Dougherty
*Assistant Examiner* — Alexander H Connor
(74) *Attorney, Agent, or Firm* — J. Nevin Shaffer, Jr.

(57) ABSTRACT

A new born temperature and heart monitor wrap apparatus and method includes a wrap where the wrap is configured such that a new born is substantially covered by the wrap when the wrap is applied to the new born. A heart monitor device is attached to the wrap and a temperature lead retainer is attached to the wrap. A substrate is provided where the wrap is removably connected to the substrate.

13 Claims, 8 Drawing Sheets

(56) References Cited

U.S. PATENT DOCUMENTS

| | | | | |
|---|---|---|---|---|
| 2011/0306945 A1* | 12/2011 | Drevik | ............... | A61F 13/5515 |
| | | | | 604/385.13 |
| 2013/0283527 A1* | 10/2013 | Houston | ............... | A41B 13/06 |
| | | | | 5/494 |
| 2014/0275742 A1* | 9/2014 | Andrew | ............... | A41B 13/06 |
| | | | | 600/27 |
| 2015/0182131 A1* | 7/2015 | Mahfouz | .............. | A61B 5/6892 |
| | | | | 600/301 |
| 2016/0073889 A1 | 3/2016 | Belsinger, Jr. et al. | | |
| 2016/0074260 A1 | 3/2016 | Belsinger, Jr. et al. | | |
| 2018/0007976 A1* | 1/2018 | Lager | ................... | A47D 15/008 |
| 2020/0037912 A1* | 2/2020 | James | ................... | A61B 5/282 |
| 2020/0281526 A1* | 9/2020 | Carpenter | .......... | A61B 5/02416 |

OTHER PUBLICATIONS

Zhu Z, Liu T, Li G, Li T, Inoue Y. Wearable sensor systems for infants. Sensors (Basel). 2015;15(2):3721-3749. Published Feb. 5, 2015. doi:10.3390/s150203721 (Year: 2015).*

* cited by examiner

NEWBORN TEMPERATURE AND HEART MONITOR APPARATUS AND METHOD

CROSS REFERENCE TO RELATED APPLICATION

This application is a national stage application of PCT patent application No. PCT/US2017/56262 filed Oct. 12, 2017 entitled "Newborn Temperature and Heart Monitor Apparatus and Method" which is supported by U.S. provisional patent application No. 62/407,724 filed on Oct. 13, 2016, of the same name. The Applicant hereby claims the benefit of the non-provisional and provisional applications under 35 U.S.C. § 119 and 120. The entire content of these applications are incorporated herein by this reference.

FIELD OF THE DISCLOSURE

The present invention pertains to a new born temperature and heart monitor wrap apparatus and method. According to one embodiment, a new born temperature and heart monitor wrap apparatus and method includes a wrap where the wrap is configured such that a new born is substantially covered by the wrap when the wrap is applied to the new born. A heart monitor device is attached to the wrap and a temperature lead retainer is attached to the wrap. A substrate is provided where the wrap is removably connected to the substrate.

BACKGROUND OF THE INVENTION

New born babies ("newborns") arrive in an environment that is, to many of them, life threatening. In particular but not by way of limitation, premature new borns suffer death at a high rate due to many factors. Two factors that play a prominent role in high new born fatalities are temperature and heart rate: too low a temperature results in hypothermia and death and too low a heart rate also can lead to death.

Thus, there is a need in the art for a system and a process that addresses the aforementioned problems in a manner that is robust and flexible so as to accommodate a full spectrum of life threatening events in the delivery room and thereafter.

It therefore is an object of this invention to provide a process and system for enabling a user to apply a heat retaining cover to a new born while at the same time simultaneously applying temperature and heart rate monitors in appropriate locations.

SUMMARY

Accordingly, the present invention pertains to a new born temperature and heart monitor wrap apparatus and method. According to one embodiment, a new born temperature and heart monitor wrap apparatus and method includes a wrap where the wrap is configured such that a new born is substantially covered by the wrap when the wrap is applied to the new born. A heart monitor device is attached to the wrap and a temperature lead retainer is attached to the wrap. A substrate is provided where the wrap is removably connected to the substrate.

All terms used herein are given their common meaning and as known in the medical profession. "Wrap" defines a material used to enclose a separate object as a jacket wraps around and covers a user. "Temperature lead retainer" describes a device for retaining a temperature lead or probe for obtaining a temperature of an object, as will be more fully described hereafter.

In one aspect, the apparatus further includes more than one heart monitor device.

In another aspect, the wrap includes a midline and the heart monitor device consists of three separate heart monitors with a first heart monitor on one side of the midline and a second and third heart monitor on another side of the midline. In one aspect, the third heart monitor is located below the second heart monitor.

In a further aspect, the new born has a posterior (back) and an anterior (front) and the heart monitor device is located on the wrap such that the heart monitor contacts the new born's posterior when the wrap is applied to the new born. In another aspect, the new born has a posterior and an anterior and the temperature lead retainer is located on the wrap such that the temperature lead retainer contacts the new born's anterior when the wrap is applied to the new born.

In one aspect, the heart monitor device extends from the wrap and is covered with a removable shield. In another aspect, the temperature lead retainer includes a temperature monitor device where the temperature monitor device extends from the wrap and is covered with a removable shield.

In a further aspect, the wrap is self adhesive.

According to another embodiment of the invention, a new born temperature and heart monitor wrap apparatus consists of a wrap where the wrap is self adhesive and configured such that a new born with an anterior and a posterior is substantially covered anteriorly and posteriorly by the wrap when the wrap is applied to the new born. A heart monitor device is attached to the wrap where the heart monitor device is located on the wrap such that the heart monitor contacts the new born's posterior when the wrap is applied to the new born. A temperature monitor device is attached to the wrap where the temperature device is located on the wrap such that the temperature device contacts the new born's anterior when the wrap is applied to the new born. A substrate is provided where the wrap is removably connected to the substrate.

In another aspect, the invention further includes more than one heart monitor device.

In one aspect, the wrap includes a midline and the heart monitor device consists of three separate heart monitors with a first heart monitor on one side of the midline and a second and third heart monitor on another side of the midline. In one aspect, the third heart monitor is located below the second heart monitor.

In one aspect, the heart monitor device extends from the wrap and is covered with a removable shield. In one aspect, the temperature monitor device extends from the wrap and is covered with a removable shield.

According to another embodiment of the invention, a new born temperature and heart monitor wrap method consists of the steps of:
a. providing a wrap where the wrap is configured such that a new born is substantially covered by the wrap when the wrap is applied to the new born; a heart monitor device attached to the wrap; a temperature monitor device attached to the wrap; and
b. providing a substrate and removably connecting the wrap to the substrate.

In another aspect, the method further includes the steps of:
a. placing a new born, with a posterior and an anterior, on said wrap such that said new born's posterior contacts said heart monitor device; and b. peeling said wrap from said substrate such that the wrap substantially covers the new born, both front and posterior, and the temperature monitor device contacts the anterior of the new born.

In another aspect, the heart monitor device extends from the wrap and is covered with a removable shield and where the temperature monitor device extends from the wrap and is covered with a removable shield and where the method consists of a first step of removing the removable shields from the heart monitor and the temperature monitor.

In one aspect, the wrap includes a midline and the heart monitor device consists of three separate heart monitors with a first heart monitor on one side of the midline and a second and third heart monitor on another side of the midline.

In a further aspect, the wrap is self-adhesive.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF EMBODIMENTS

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described method may be altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated. For example, further insubstantial approximations of the process and/or method are also considered within the scope of the method described herein.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

It should also be noted that a plurality of hardware and software based devices, as well as a plurality of different structural components, may be utilized to implement the invention. Furthermore, and as described in subsequent paragraphs, the specific configurations illustrated in the drawings are intended to exemplify embodiments of the invention and that other alternative configurations are possible.

The invention is properly understood with reference to FIGS. 1-8. One embodiment of the present invention is illustrated by way of example in FIG. 1. With specific reference to FIG. 1, new born temperature and heart monitor wrap 10 includes wrap 12. Wrap 12 is preferably a "self-adhesive" wrap as is known in the art such as a plastic film made of semipermeable low density polyethylene (LDPE), such as plastic food wraps for example only and not by way of limitation. Wrap 12 is configured such that a new born 14 (not shown in FIG. 1; see FIG. 3) is substantially covered by wrap 12 when the wrap 12 is wrapped around the new born 14 (See eg FIGS. 3 and 4). In another example only and not by way of limitation, such configuration can be such that the wrap 12 is perforated at multiple locations to allow for substantial coverage of the new born 14's extremities or limbs, i.e., arms, legs, feet.

Figure 1:
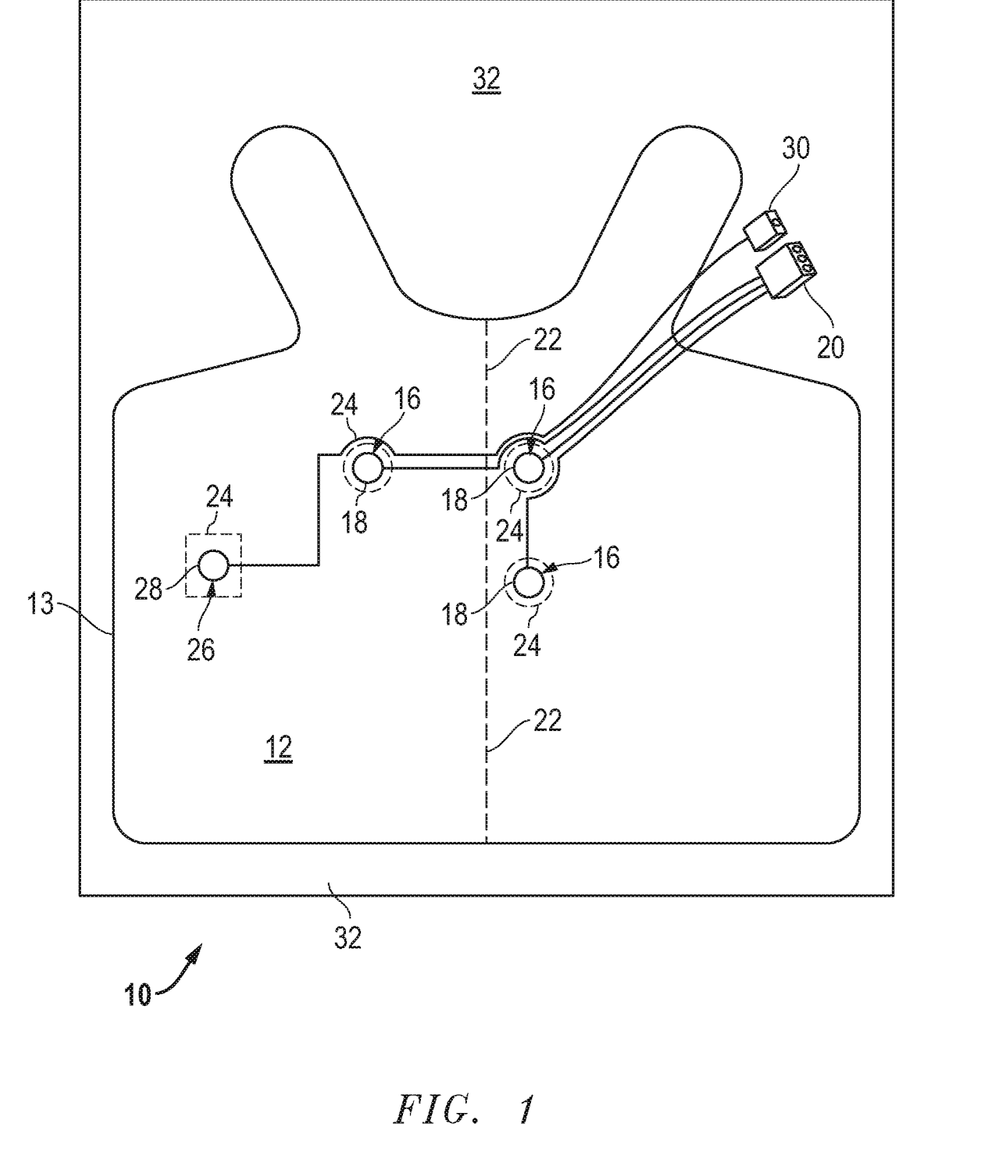
FIG. 1 is a top view of the new born temperature and heart monitor wrap according to one embodiment.

Heart monitor device 16 is attached to wrap 12. Heart monitor device 16 is any heart monitor now known or hereafter developed for monitoring heart rate such as for example only and EKG heart monitor. As illustrated, heart monitor device 16 includes a heart monitor lead 18 attached to wrap 12 with a heart monitor connector 20 attached to the heart monitor lead 18. Heart monitor connector 20 is configured for connecting with a heart monitor display (not shown) as is known in the art and not described more fully hereafter.

In a preferred embodiment, wrap 12 includes a "midline" 22 and three leads 18, with one lead on each side of the midline 22 and a third lead 18 below one of the leads on one side of the midline 22. In one aspect of the invention, leads 18 are covered with a removable shield 24. Removable shield 24 covers and protects leads 18 prior to placing a new born 14 on wrap 12, as will be discussed more fully hereafter with regard to FIGS. 3 and 4. In one aspect the leads 18 include an adhesive (not shown for clarity) such that after removal of the shields 24, the leads 18 adhere to the new born 14 when the new born is laid onto wrap 12.

Temperature monitor device 26 is any temperature monitor now known or hereafter developed for monitoring body temperature. As with the heart monitor device 16, temperature monitor device 26 preferably includes temperature monitor lead 28 connected with a temperature probe connector 30. Temperature probe connector 30 is configured for connection with a temperature display (not shown) as are known in the art.

Figure 3:
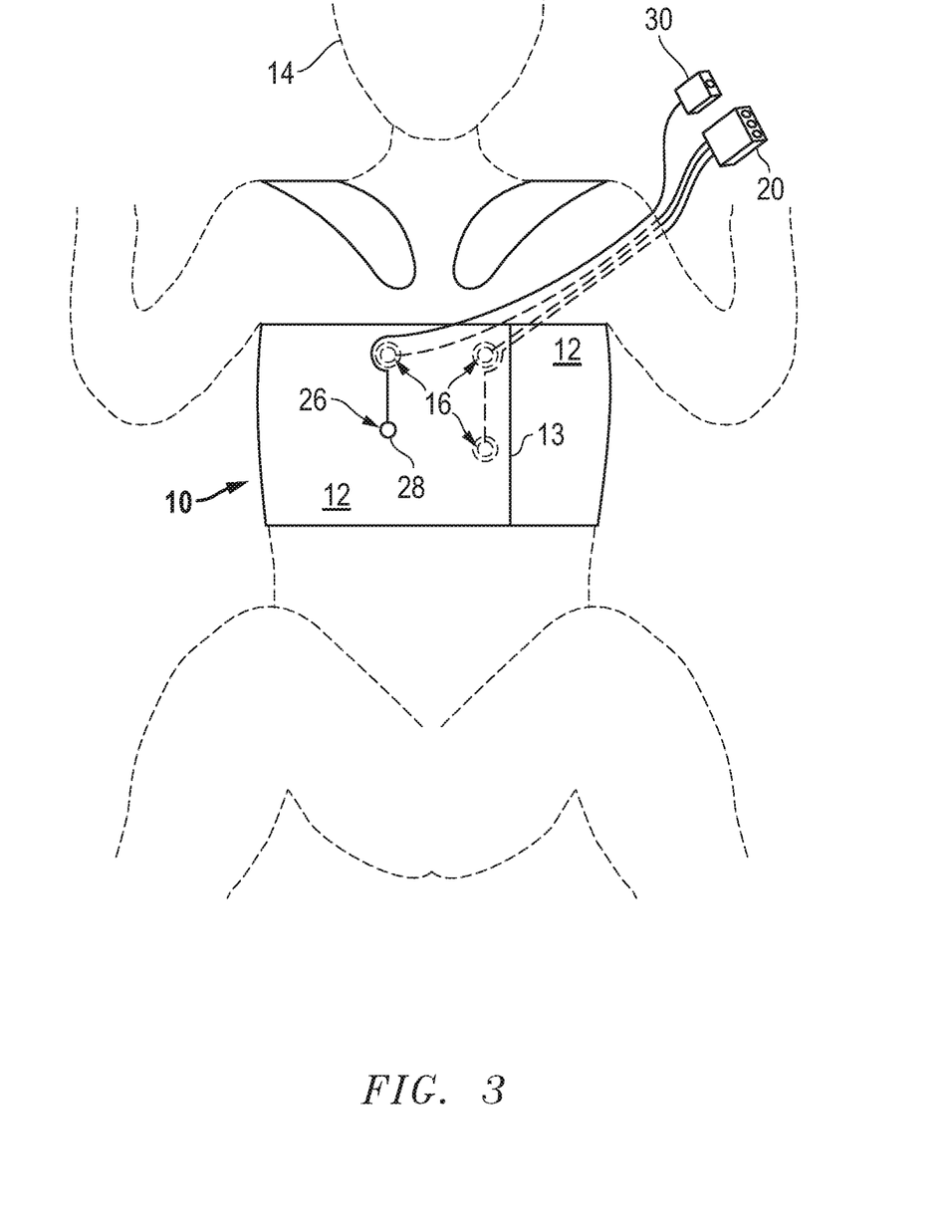
FIG. 3 is a top view of the invention of FIG. 1 with the wrap of the invention surrounding a new born baby.

As more clearly shown in FIG. 3, preferably temperature monitor lead 28 is attached to wrap 12 such that when a new born 14 is laid posterior down on wrap 12 and wrap 12 is wrapped around new born 14, temperature monitor lead 28 is positioned on the anterior of new born 14. Thus, as illustrated, while heart monitor leads 18 are preferably located on the posterior of the new born 14 below the neck and centered along midline 22, the temperature monitor lead 28 is preferably spaced apart from midline 22 nearer the edge 13 of wrap 12.

Figure 2:
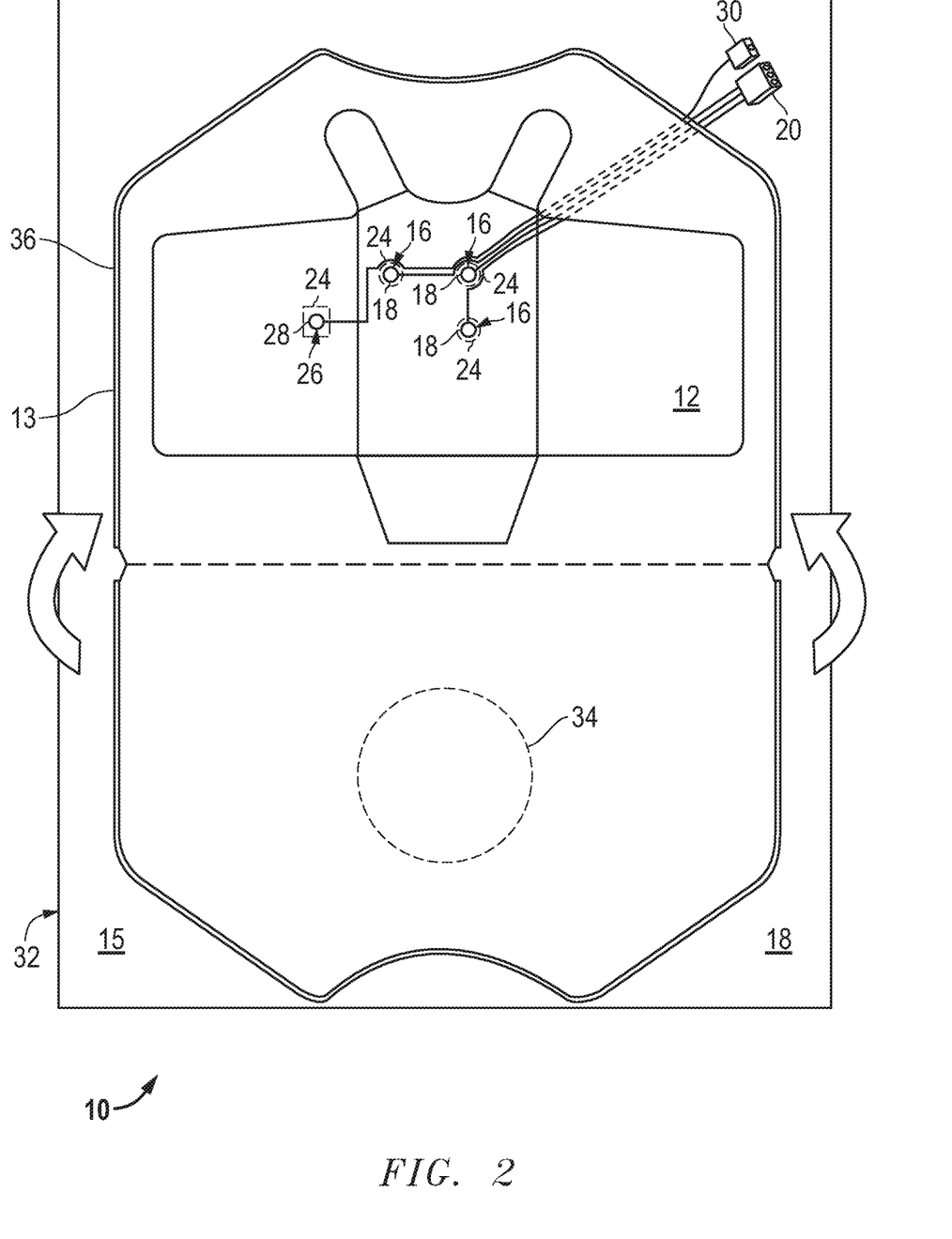
FIG. 2 is a top view of the invention of FIG. 1 according to another embodiment.

As shown in FIGS. 1 and 2, wrap 12 is removably attached to substrate 32. Substrate 32 serves as a transport and delivery vehicle for wrap 12. Plastic wrap that is self adhesive is extraordinarily difficult to apply without bunching and sticking to itself or other things. The inventors determined that substrate 32 is a unique solution to this problem. Substrate 32 is any useful light weight sturdy material, such as cardboard or heavy gauge paper, for example only. Wrap 12 is attached to substrate 32 by any useful means, such as tape or hook and loop material, for example only, and held in the required extended, flat, position as shown in FIGS. 1 and 2 prior to use. In use, new born 14 is placed back down on top of wrap 12. At that point, wrap 12 is peeled off of substrate 32, or vice versa, and wrapped around new born 14 while simultaneously applying heart monitor device(s) 16 and temperature monitor device 26 in exactly the correct, preferred, place on new born 14. Thereafter, the fully wrapped and monitored new born 14 may be moved and the substrate 32 discarded. Multiple prepackaged substrates 32 with the wrap 12 and monitors attached may be assembled in sterile environments, kept that way, and used one after another when needed.

Figure 4:
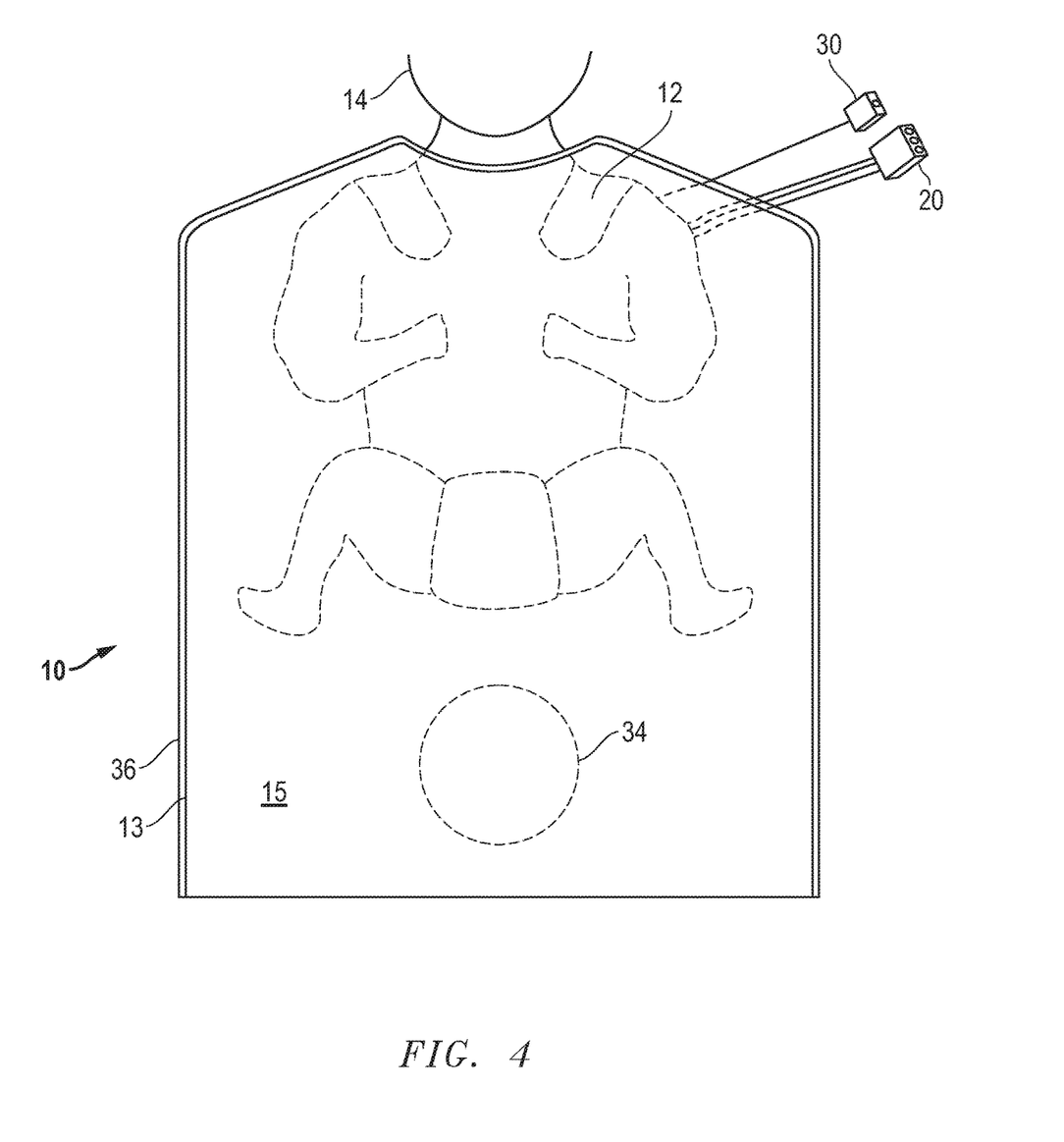
FIG. 4 is a top view of the invention of FIG. 2 enclosing a very small new born baby.

Referring now to FIG. 2, in another embodiment, wrap 12 is configured to essentially enclose the new born 14 (not shown; see FIG. 4). Essentially, the configuration of wrap 12 as shown in FIG. 1 is attached to a larger wrap 15. Here the wrap 12 is applied to the new born 14 as described above and then the new born 14 is enclosed within a larger portion of wrap 12, larger wrap 15, as shown more clearly in FIG. 4. This configuration is preferred when the new born 14 is quite premature e.g. twenty-two week to thirty weeks, and smaller for example. When the new born 14 is older, e.g. thirty weeks to term, and larger then the embodiment illustrated in FIG. 1 may be more appropriate and effective. Certainly, in any form, when used with a new born 14 the ameliorative effects of the present invention are obtained.

FIG. 2 shows a feature of that embodiment, access port 34. Access port 34 is a re-sealable opening in larger wrap 15. When wrapped around a new born as shown in FIG. 4, access port 34 provides direct physical access to the new born 14 without interference of wrap 12 or 15. Other elements of the invention are the same as more fully described above with regard to FIG. 1 and are so numbered.

Wrap 12 is self-adhesive preferably but may be sealed together by any means deemed useful such as by a "zip lock" connector 36, where the edges 13 interlock when pressed together, for example only, around the edges 13 of wrap 12 and/or 15.

FIG. 3 illustrates the present invention as shown in FIG. 1 used with a new born 14 that is larger such as ones thirty weeks to term. FIG. 4 illustrates the present invention as shown in FIG. 2 used with a new born 14 that is smaller and younger such as twenty two weeks to thirty weeks.

Figure 5:
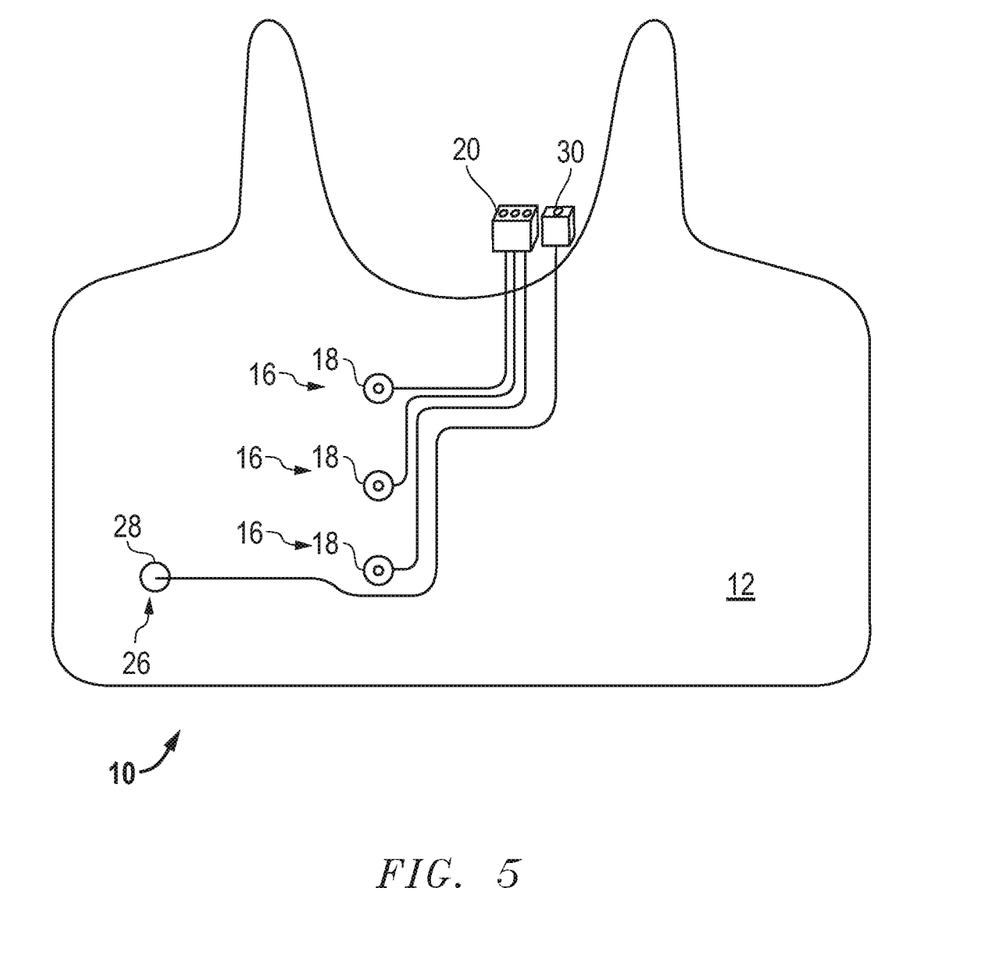
FIG. 5 is a top view of the invention of FIG. 1 with another configuration of heart monitors.

FIG. 5 illustrates another embodiment of the invention where the heart monitor devices 16 are arranged in a line, one over the other, as may be preferred in some instances.

Figure 6:
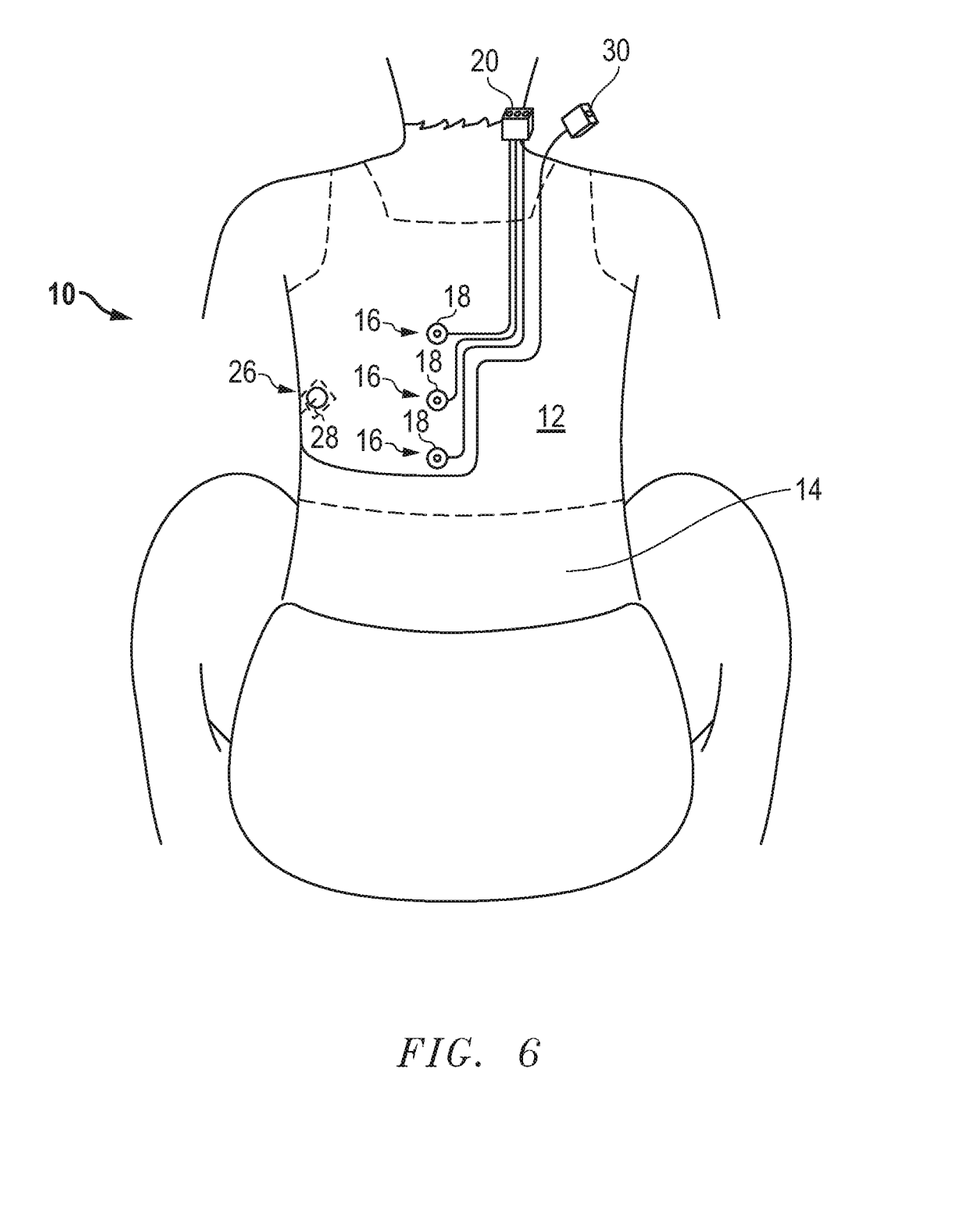
FIG. 6 is a top view of the invention of FIG. 5 wrapped around a new born baby as seen from the posterior of the baby.

FIG. 6 shows the invention of FIG. 5 showing the wrap 12 applied to a new born baby 14 and illustrating the alignment of the heart monitor devices 16 in a line, one over the other.

Figure 7:
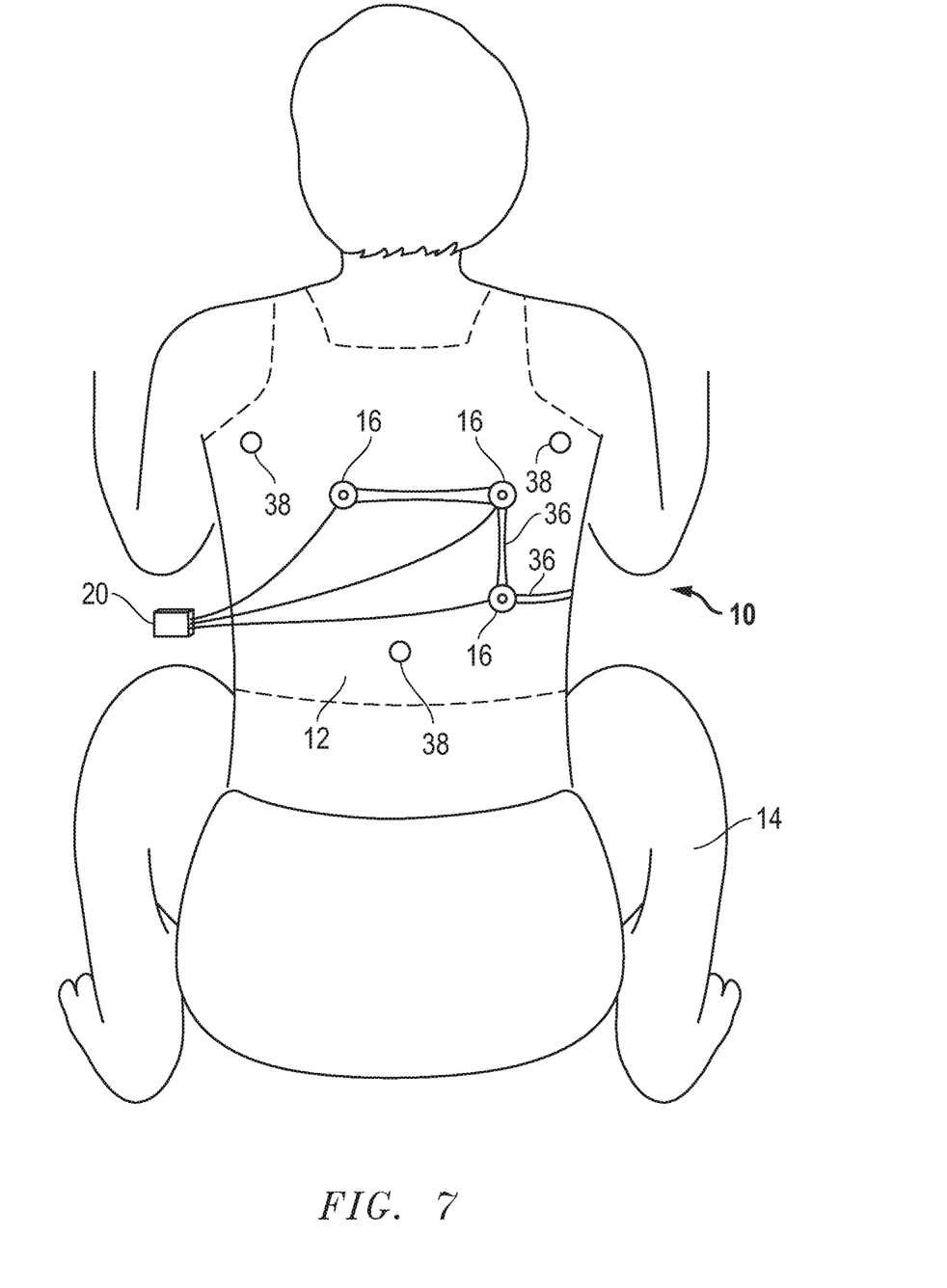
FIG. 7 is a top view of the invention of FIG. 1 showing another configuration where the heart monitor and temperature leads extend from the side of the wrap.

FIG. 7 illustrates another configuration where the heart monitor lead 16 and the heart monitor connector 20 extend from the side of the wrap 12 not, as previously illustrated, near the head of the baby 14 as may be preferred. Also, FIG. 7 shows another arrangement where no temperature monitor connector 30 or temperature monitor lead 28 or temperature monitor devices 26 are provided. In this embodiment, on site temperature monitor devices connected with temperature leads, as are common in hospital environments, are connected to wrap 12 by way of a temperature lead retainer 38. In this case, there are multiple temperature lead retainers 38 in various locations on wrap 12 which enables a user to connect an on site temperature lead wherever best for the situation and position of the baby 14. For example, temperature probes or leads are attached to a different location on a resuscitation table than the heart probe, so having the temperature probe connector 30 at the same place as the heart monitor connector 20 (See eg FIGS. 1-4) causes problems when attaching the temperature probe connector 30. The connection with temperature lead retainer 38 is accomplished in any known manner, such as a sticky substance on a patch or a mechanical connector, as are known in the art. The purpose is to provide a sure way to hold a temperature lead in a selected position, one of many, on wrap 12.

Figure 8:
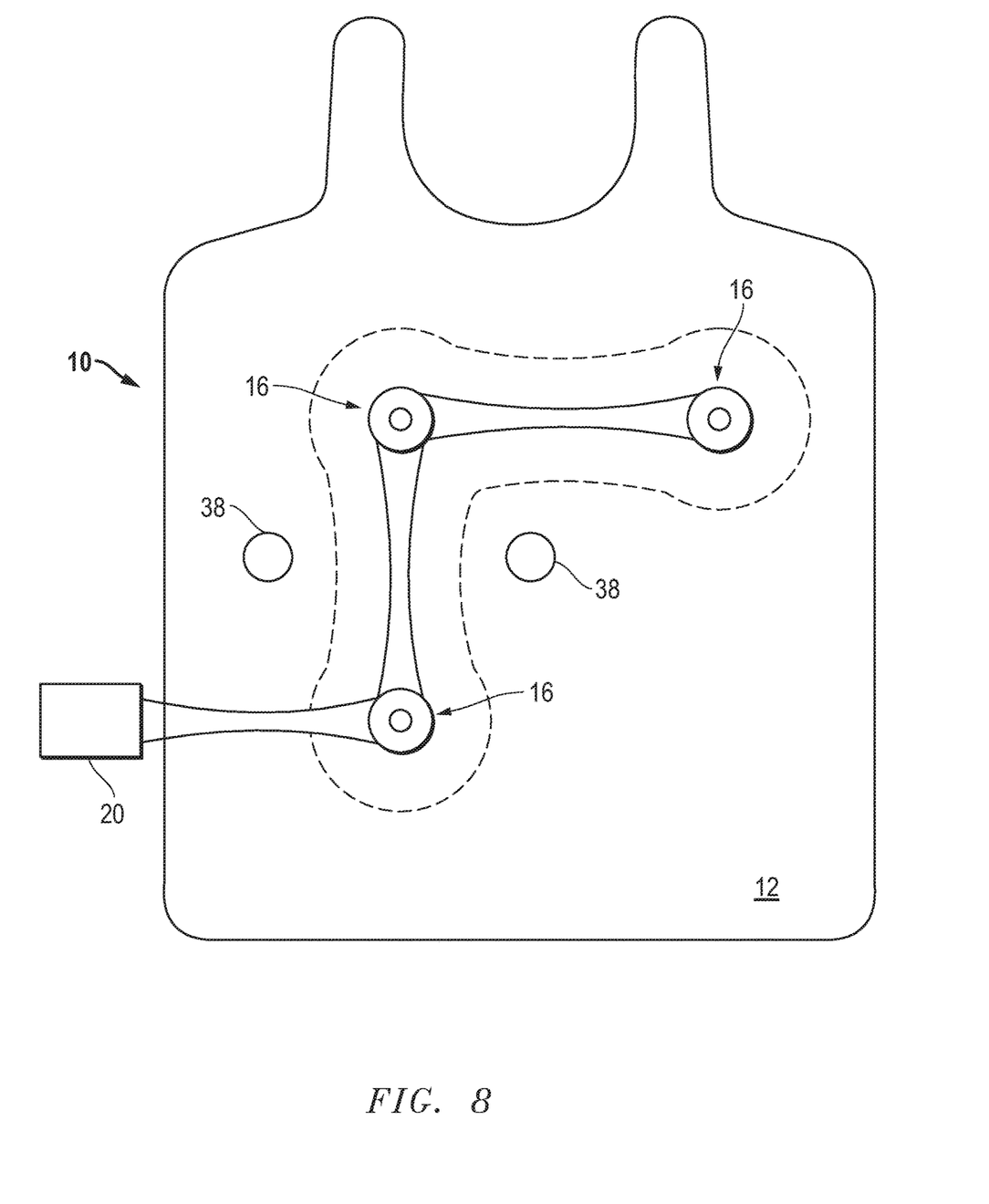
FIG. 8 is a top view of the invention of FIG. 1 where the temperature monitor lead is removed and replaced with a number of temperature lead retainers.

FIG. 8 illustrates a configuration of heart monitor devices 16 as above along with a temperature lead retainer 38 for holding an on site temperature probe (not shown) as described with regard to FIG. 7.

By way of further explanation, the present invention may be better understood by the following description. Immediately after birth, an infant's heart rate ("HR") must be assessed as accurately and quickly as possible to determine if any interventions are needed. Chest compressions should be used if the HR is less than 60 bpm after 30 seconds of positive-pressure ventilation. Overestimations of HR might result in delayed interventions while underestimations of HR might result in the initiation of resuscitation when it is not required. An increase in the newborn's HR is considered the most sensitive indicator of a successful response to each intervention. Therefore, a rapid, reliable, continuous, and accurate method to measure a newborn's HR is critically important.

Resuscitation guidelines traditionally recommend assessing a newborn's HR by 'listening to the precordium with a stethoscope and feeling for pulsations at the base of the umbilical cord'. Pulse oximetry ("PO") was recommended as an adjunct to provide a noninvasive, rapid, and continuous assessment of HR during resuscitation. However, research suggests that providers may not assess HR accurately by auscultation or palpation, and PO may underestimate HR.

Guidelines updated in 2015 recommend the use of 3-lead electrocardiography (ECG). Early application of ECG electrodes during high-risk deliveries can provide the resuscitation team with a continuous/audible HR and its use may improve the timeliness of appropriate critical interventions.

The present invention proposes a novel neonatal ECG and temperature monitor that incorporates, in one embodiment, three ECG electrodes and a thermometer sensor into a single easy to apply plastic film made of semipermeable low density polyethylene (LDPE), designed for placement on a newborn's back. Each lead is connected by wiring to its corresponding connector on an ECG and temperature monitor. In one configuration, the ECG electrodes are made by replacing the Ag coated plate with an Ag nanoparticle that interacts with the AgCl hydrogel. By decreasing the size of the metal particle, the surface contact between the electrode and electrolyte is increased. This improves signal transmission by decreasing impedance and noise. Furthermore, it reduces the bulkiness of the ECG lead, resulting in a low-profile design that conforms to the newborn's skin.

A key advantage of the present invention is that it incorporates other standard monitoring and care procedures. A newborn's ability to maintain a stable body temperature in a normal environment is another important indicator of their overall health. The addition of a temperature sensor onto the LDPE film provides continuous temperature monitoring. While LDPE bags and wraps have been used in the delivery room to help prevent hypothermia in newborns Applicants' invention is a significant and unique improvement. As shown in FIGS. 1-4, the invention calls for a film design that allows for it to be wrapped around the baby in an easy to use fail proof manner so as to prevent evaporative heat loss. The addition of a temperature probe and the use of LDPE in the construction of the device reduces costs of care and frees up members of the medical team to perform other lifesaving tasks.

Another advantage, and prior art problem solved by the present invention, of using LDPE is its self-retaining capacities, which helps keep the wrap from slipping. Also the hydrogel base, when present, of the electrode reinforces the lead position. As a result, the need for adhesive is eliminated. This is an improvement over traditional electrode designs, particularly when used in premature babies, whose outer layer of skin (the epidermis) may be very thin, making them susceptible to skin breakage when the adhesive is removed.

Further, the pre-attached electrode and temperature array of the present invention simplifies the application of electrodes and temperature monitor device. The LDPE sheet with pre-attached sensors is attached to the substrate for ease of movement and the substrate is simply placed on the crib/table. The newborn is placed posterior down on top of the wrap immediately after delivery. The sensor shields having been removed, the sensors immediately contact the newborn in the precisely correct position, preferably one on either side of the midline and one below. This reduces the delay in acquisition of an ECG signal due to individual lead placement and provides faster response time for the medical team. Furthermore, the placement on the baby's posterior allows for maximum exposure of the chest area during resuscitation efforts. The wrap is then peeled off of the supporting substrate, or vice versa, and wrapped around the newborn. This then positions the temperature monitor device in the precisely correct position on the newborn's front.

Still further, in a preferred embodiment, the device is disposable, which reduces up front costs, minimizes the risk of cross-contamination between patients and eliminates the need for lengthy sterilization processes.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. A new born temperature and heart monitor wrap apparatus comprising:
   a. a wrap wherein said wrap is a self adhesive plastic film configured to adhere to and cover a new born when said wrap is applied to said new born;
   b. a heart monitor device attached to said wrap wherein said heart monitor device is located on said wrap such that said heart monitor is configured to contact said new born's posterior when said wrap is applied to said new born;
   c. a temperature monitor device attached to said wrap wherein said temperature device is located on said wrap such that said temperate device contacts said new born's anterior when said wrap is applied to said new born;
   d. a substrate wherein said wrap is removably connected to said substrate and said substrate retains said wrap in an extended position prior to application; and
   e. an extended section of said wrap connected with said wrap wherein said extended section is configured to enclose the wrap and the newborn within the extended section and wherein the extended section includes an access port configured for direct access to the newborn.

2. The apparatus of claim 1, further including more than one heart monitor device.

3. The apparatus of claim 1 wherein said wrap includes a midline and said heart monitor device consists of three separate heart monitors with a first heart monitor on one side of said midline and a second and third heart monitor on another side of the midline.

4. The apparatus of claim 3 wherein said third heart monitor is located below said second heart monitor.

5. The apparatus of claim 1 wherein said wrap includes a midline and said beat monitor device consists of three separate heart monitors wherein said three heart monitor devices are arranged in a line all on one side of the midline.

6. The apparatus of claim 1 wherein said temperature monitor device extends from said wrap and is covered with a removable shield.

7. A new born temperature and heart monitor wrap method comprising
   a. providing a wrap wherein said wrap is self adhesive plastic configured to adhere to and cover a newborn when said wrap is applied to said new born; a heart monitor device attached to said wrap wherein said heart monitor device is located on said wrap such that said heart monitor device is configured to contact said new born's posterior when said wrap is applied to said new born; a temperature monitor device attached to said wrap wherein said temperature device is located on said wrap such that said temperature device contacts said new born's anterior when said wrap is applied to said new born; and a substrate wherein said wrap is removably connected to said substrate and an extended section of said wrap connected with said wrap wherein said extended section is configured to enclose the wrap and the newborn within the extended section and wherein the extended section includes an access port configured for direct access to the newborn; and
   b. providing a substrate and removably connecting said wrap to said substrate wherein said substrate retains said wrap in an extended position prior to application.

8. The method of claim 7 wherein said wrap is configured to cover a new born when applied such that said temperature monitor device contacts said new born's posterior.

9. The method of claim 7 wherein said heart monitor device extends from said wrap and is covered with a removable shield and wherein said temperature monitor device extends from said wrap and is covered with a removable shield and wherein said method consists of a first step of removing said removable shields from said heart monitor and said temperature monitor.

10. The method of claim 7 wherein said wrap includes a midline and said heart monitor device consists of three separate heart monitors with a first heart monitor on one side of said midline and a second and third heart monitor on another side of the midline.

11. The method of claim 10 wherein said third heart monitor is located below said second heart monitor.

12. The method of claim 7 further including more than one heart monitor device.

13. The method of claim 7 wherein said wrap includes a midline and said heart monitor device consists of three separate heart monitors wherein said three heart monitor devices are arranged in a line all on one side of the midline.

\* \* \* \* \*

UNITED STATES PATENT AND TRADEMARK OFFICE
CERTIFICATE OF CORRECTION

PATENT NO. : 11,324,403 B2
APPLICATION NO. : 16/382819
DATED : May 10, 2022
INVENTOR(S) : Fabien Gabriel Eyal et al.

Page 1 of 1

It is certified that error appears in the above-identified patent and that said Letters Patent is hereby corrected as shown below:

In the Claims

Column 8, Line 18: "said temperate device" should read --said temperature device--.

Column 8, Line 39: "said beat monitor device" should read --said heart monitor device--.

Signed and Sealed this
Twenty-seventh Day of August, 2024

Katherine Kelly Vidal
*Director of the United States Patent and Trademark Office*